(12) United States Patent
Kim

(10) Patent No.: US 11,464,822 B2
(45) Date of Patent: Oct. 11, 2022

(54) MANUFACTURING METHOD OF HERBAL MEDICINE PROCESSED FOOD

(71) Applicant: Arang Farm Co., Ltd., Jeollanam-do (KR)

(72) Inventor: Arang Kim, Seoul (KR)

(73) Assignee: Arang Farm Co., Ltd., an agricultural company, Jeollanam-do (KR)

( * ) Notice: Subject to any disclaimer, the term of this patent is extended or adjusted under 35 U.S.C. 154(b) by 64 days.

(21) Appl. No.: 17/105,536

(22) Filed: Nov. 26, 2020

(65) Prior Publication Data

US 2022/0160803 A1    May 26, 2022

(51) Int. Cl.

| | |
|---|---|
| *A61K 36/533* | (2006.01) |
| *A61K 9/00* | (2006.01) |
| *A61K 36/8945* | (2006.01) |
| *A61K 36/81* | (2006.01) |
| *A61K 36/539* | (2006.01) |
| *A61K 36/185* | (2006.01) |
| *A61K 36/899* | (2006.01) |
| *A61K 36/481* | (2006.01) |
| *A61K 36/488* | (2006.01) |
| *A61K 36/30* | (2006.01) |
| *A23L 33/105* | (2016.01) |
| *A23P 10/28* | (2016.01) |
| *A23L 3/40* | (2006.01) |
| *A61K 9/14* | (2006.01) |

(52) U.S. Cl.
CPC .............. *A61K 36/533* (2013.01); *A23L 3/40* (2013.01); *A23L 33/105* (2016.08); *A23P 10/28* (2016.08); *A61K 9/0053* (2013.01); *A61K 9/14* (2013.01); *A61K 36/185* (2013.01); *A61K 36/30* (2013.01); *A61K 36/481* (2013.01); *A61K 36/488* (2013.01); *A61K 36/539* (2013.01); *A61K 36/81* (2013.01); *A61K 36/899* (2013.01); *A61K 36/8945* (2013.01); *A23V 2002/00* (2013.01); *A61K 2236/15* (2013.01); *A61K 2236/17* (2013.01)

(58) Field of Classification Search
None
See application file for complete search history.

(56) References Cited

FOREIGN PATENT DOCUMENTS

KR    10-1808584 B2    8/2017

*Primary Examiner* — H. Sarah Park
(74) *Attorney, Agent, or Firm* — Nicholas Park

(57) ABSTRACT

Exemplary embodiments relate to a manufacturing method of herbal medicine processed food. The method comprises (a) drying raw materials of *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi, and *Lithospermum erythrorhizon* by means of vacuum drying, wherein the drying temperature is 20 to 80° C., (b) grinding each of the vacuum-dried raw material of the step (a) to produce powder, (c) shaping mixture of powder of the step (b) into a round shape.

5 Claims, No Drawings

MANUFACTURING METHOD OF HERBAL MEDICINE PROCESSED FOOD

BACKGROUND

1. Field

Example embodiments relate to a manufacturing method of herbal medicine processed food capable of maximizing the convenience of food use and that have excellent nutrition retention.

2. Description of the Related Art

While the processed food market is increasing due to the increase in women's economic activities, the increase in single-person households, and the aging population, the growth of the health functional food market is also accelerating rapidly as interest in health increases.

Accordingly, the development of processed foods using natural substances such as domestic food, pesticide-free, non-antibiotic, additive-free, non-coloration ingredients, and non-genetically modified foods is actively ongoing.

In the process of manufacturing processed foods, natural drying of crops that are raw materials of processed foods has the advantage of excellent supply and demand of raw materials due to the high retention of nutritional ingredients and the freshness of raw materials. On the other hand, natural drying process requires drying in the natural state of the outdoors, so it has a significant space share, is heavily affected by the climate, has a long drying time, and has difficulties in mass production.

Hot-drying method and freeze-drying method are introduced to solve the above-mentioned problem. The hot drying method is dried at a high temperature of 80° C. or higher, and has the advantage of a shorter drying time and less affected by the climate compared to the natural drying method, but there are disadvantages of significantly losing nutrients and their original taste.

In addition, The freeze-drying method has the advantage of a shorter drying time than the natural drying method and less affected by the climate, but there is a disadvantage that the supply and demand capacity of raw material decreases because freshness of the raw materials decreases significantly as the shelf life of the raw materials becomes unclear compared to both the natural drying method and the hot-drying method.

On the other hand, herbal medicines rich in various nutrients are usually easily decayed and deteriorated in hot and humid environment, so it essentially requires a drying process that lowers the moisture inside the medicines for longer storage period, and there is a problem that it requires cumbersome process such as brewing or taking powdered herb to take medicine induce people to be reluctant to take herbal medicines.

Accordingly, by applying a drying process that minimizes the loss of nutrients in herbal medicines, a method of manufacturing processed foods for herbal medicines is required to improve the nutritional retention characteristics of herbal medicines and maximize the convenience of food use.

RELATED ART DOCUMENTS

Patent Documents

Patent Document 1: Korean Patent Registration No. 10-1808584

SUMMARY OF THE INVENTION

To solve the problems mentioned above, example embodiments relate to the manufacturing method of herbal medicine processed foods that have excellent nutritional properties and maximize the convenience of food use.

Additional example embodiments will be set forth in part in the description which follows and, in part, will be apparent from the description, or may be learned by practice of the example embodiments.

According to an example embodiment, A manufacturing method of herbal medicine processed food is provided. The method comprises (a) drying raw materials of Leonurus japonicus Houtt, Dioscorea bulbifera, Solanum nigrum L, Scutellaria baicalensis, Akebiae Caulis, corn silk, Astragalus membranaceus, Pueraria lobata Ohwi, and Lithospermum erythrorhizon by means of vacuum drying, wherein the drying temperature is 20 to 40° C.; (b) grinding each of the vacuum-dried raw material of the step (a) to produce powder; (c) shaping mixture of powder of the step (b) into a round shape.

The method may comprise drying Leonurus japonicus Houtt, Dioscorea bulbifera, Solanum nigrum L at a temperature in a range of 20 to 25° C.; drying Scutellaria baicalensis, Akebiae Caulis, corn silk, Astragalus membranaceus at a temperature in a range of 30 to 35° C.; drying Pueraria lobata Ohwi, Lithospermum erythrorhizon at a temperature in a range of 35 to 40° C.

The method may comprise drying by means of hot air at a vacuum pressure in a range of 30 to 100 kPa.

The method may comprise a particle diameter of the powder is in a range of 100 to 500 μm.

The method may comprise the mixture of powder in the step (c) satisfied a mixed ratio(w/w) of the Leonurus japonicus Houtt, Dioscorea bulbifera, Solanum nigrum L, Scutellaria baicalensis, Akebiae Caulis, corn silk, Astragalus membranaceus, Pueraria lobata Ohwi, and Lithospermum erythrorhizon is 1:1.3 to 1.8:1.3 to 1.8:0.8 to 1.2:0.5 to 1.2:0.5 to 1.2:0.5 to 1.2:0.5 to 1.2:0.8 to 1.1.

Further areas of applicability will become apparent from the description provided herein. The description and specific examples in this summary are intended for purposes of illustration only and are not intended to limit the scope of the present disclosure.

DETAILED DESCRIPTION

Reference will now be made in detail to example embodiments, examples of which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures. In order to clearly explain the invention in the drawing, the non-explanatory part was omitted.

The terms or words used in the description and scope of claims of this invention shall not be construed in a conventional or dictionary sense, and shall be construed as meaning and concept consistent with the technical ideas of this invention, on the basis of the principle that the inventor can adequately define the concept of the term in order to explain his own invention in the best way.

For the whole of the specifications of this invention, when a part is said to "comprise" a component, this means that it may contain more other components, rather than exclude other components, unless there is a particularly contrary article.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

When the term "round shape" is used in this specification, it is intended that that associated feature's shape has substantially circular shape. For example, "round shape" may include two-dimensional round shape (such as circle, elliptic circle) and three-dimensional round shape (such as round sphere, elliptic sphere)

Hereinafter, the present invention will be described in more detail to help in understanding the present invention. According to the invention, a method of manufacturing processed herbal medicine products is provided. The manufacturing method of the herbal processed food comprises (a) drying raw materials of *Leonurus japonicus* Houtt, *Dioscorea bulbifera, Solanum nigrum* L, *Scutellaria baicalensis, Akebiae Caulis*, corn silk, *Astragalus membranaceus, Pueraria lobata* Ohwi, and *Lithospermum erythrorhizon* by means of vacuum drying, wherein the drying temperature is 20 to 40° C.;

(b) grinding each of the vacuum-dried raw material of the step (a) to produce powder;

(c) shaping mixture of powder of the step (b) into a round shape.

In the conventional drying process of processed food, in the case of natural drying of the crop that is the raw material of the processed food, the nutrients can be maintained and the freshness of the raw material is excellent, so the raw material supply ability is excellent, but it is dried outdoors in natural conditions. Therefore, the space occupancy is quite high, it is affected by the climate, the drying time is long, and mass production is difficult.

The high-temperature drying method and the freeze-drying method are designed to solve this problem. In the case of the high-temperature drying method, it is a method of drying at a high temperature of 80° C. or higher, and the drying time is shorter and less affected by the climate than the natural drying method. Also, there is a disadvantage in that nutritional components and natural taste are significantly lost.

In addition, in the case of the freeze-drying method, the drying time is shorter than that of the natural drying method and has the advantage of receiving less nutrition from the climate.

Compared to both the natural drying method and the high-temperature drying method, the raw material can be stored longer and the production period becomes unclear, so the freshness of the raw material is remarkably lowered and the raw material supply capacity is deteriorated.

On the other hand, since herbal medicines rich in various nutrients are usually easily spoiled and deteriorated in high temperature and humid places, they are essentially subjected to a drying process to lower the moisture content for storage, and when ingested, they must be boiled down or powdered. There was a problem that busy modern people were reluctant to consume because of the hassle of doing it.

Accordingly, in the present invention, it is intended to provide a method of manufacturing a processed herbal product that has excellent nutritional properties of the herbal medicine and maximizes the convenience of edible food.

The nine raw materials used in the present invention may be used as herbal medicine. The herbal medicine is a natural product used for the prevention or treatment of diseases based on the basic theory of oriental medicine, and may be collected from animals, plants, or minerals.

The *Leonurus japonicus* Houtt is a biennial herbaceous plant belonging to the Lamiaceae family. It is known to have efficacy in hemostatic action, blood pressure lowering, cardiac action, diuretic action, anti-cancer action, angina pectoris, menstrual hyperactivity, postpartum bleeding, menstrual pain, and nervous breakdown. As a specific example, in the present invention, the above-ground portions (stems and leaves) of *Leonurus japonicus* Houtt may be used, but the present invention is not limited thereto.

The *Dioscorea bulbifera* is a perennial vine plant belonging to the hemp family, and unlike the generally known long hemp, its shape is round, has a lower moisture content than other hemps, and contains a large amount of mucin, protecting the stomach wall. It is known to be effective in prevention peptic gastric ulcer, too. As a specific example, in the present invention, a tuber of a *Dioscorea bulbifera* may be used, but the present invention is not limited thereto.

The *Solanum nigrum* L is an annual herbaceous plant belonging to the eggplant family and is known as a medicinal herb that controls kidney and bladder deterioration and has excellent anticancer effects. The ingredients of the *Solanum nigrum* L contain various alkaloids such as solanine and solasonin, and are most often contained in fruits, and contain ingredients such as steroids, rutin, and saponin. It is effective in killing germs such as typhus, staphylococcus aeruginosa, Pseudomonas aeruginosa, red lichen, and *E.*

*coli*, and eliminating inflammation. As a specific example, in the present invention, the fruit of *Solanum nigrum* L may be used, but is not limited thereto.

The *Scutellaria baicalensis* is a perennial herbaceous plant belonging to the Lamiaceae, and is known to have anti-inflammatory, sedative, antioxidant, and dermatitis treatment effects as pharmacological effects. As a specific example, in the present invention, a *Scutellaria baicalensis* root may be used, but the present invention is not limited thereto.

The *Akebiae Caulis* is a dried stem of a vine and a plant vine (*Akebiae Quinata* Decne.), contains 11 kinds of akebosides, diuretic, cardiac action, blood pressure elevation, anti-inflammatory action, gastric juice secretion suppression. It is a medicinal herb with strong efficacy. As a specific example, in the present invention, it may be used that the bark of the vine stem is removed, but is not limited thereto.

The corn silk is a female flower of corn having a form of fine thread tangled with each other at the ends of corn, has a diuretic effect, acts to lower blood pressure, and is also used in the treatment of enlarged prostate. In addition, corn silk is rich in vitamins, so it has a soothing effect on sensitive skin, and corn silk contains flavonoids, so it has an antioxidant effect.

The *Astragalus membranaceus* is a perennial herbaceous plant belonging to the legume family, and its roots are mainly used as medicinal materials in oriental medicine. It has liver protection, immunity promotion, anti-cancer, antibacterial, antioxidant, tonic, diuretic, etc. It is known to contain a large amount of polyphenolic substances and isoflavonoids. As a specific example, in the present invention, a root of *Astragalus* may be used, but the present invention is not limited thereto.

The *Pueraria lobata* Ohwi is a root of arrowroot belonging to the genus *Pueraria* genus of the leguminosae, and its main ingredients are daidzain, daidzin, genistein, paracuma. There are puerarine, quercetin, calcium, iron, magnesium, phosphorus, potassium, and vitamin B2. Also, from ancient times, it has been used as an antidote, anti-emetic, antispasmodic, cardiac, pain reliever, cleansing agent, antiperspirant, antipyretic, milk secreting agent, hypoglycemic agent, and blood pressure lowering agent.

*Lithospermum erythrorhizon* is a perennial plant belonging to the genus *Lithospermum* of Borraginaceae, and is a representative plant containing shikonin and its derivatives in its roots. It is used in formulations for anti-inflammatory, detoxifying and antipyretic purposes. *Lithospermum erythrorhizon* is used as an ointment for swelling, burns, frostbite eczema and hemorrhoids due to its antiseptic and anti-inflammatory action. Recently, it has been used as a cosmetic raw material and high-quality natural dye. As a specific example, the roots of *Lithospermum erythrorhizon* may be used in the present invention, but the present invention is not limited thereto.

In the present invention, the nine kinds of raw materials are not limited to the area of use and various organs and tissues such as trees, leaves, flowers, stems, roots, fruits and seeds of each raw material can be used.

The herbal medicinal processed food manufactured according to the manufacturing method of the present invention can provide the pharmacological effect of the active ingredients contained in each raw material by including all of the above nine raw materials.

In particular, the processed herbal medicine food has the effect of enhancing antioxidant activity by including the active ingredients contained in the nine raw materials. As a specific example, the antioxidant activity measurement is DPPH (1,1-diphenyl-2-picrylhydrazyl) free radical scavenging activity test, ABTS (2,2'-azinobis (3-ethylbenzothiazoline-6-sulfonic acid)) cationic radical scavenging activity test. It may be performed through, but is not limited thereto.

According to an embodiment of the present invention, the step (A) may be a step of vacuum drying the nine materials of *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi and *Lithospermum erythrorhizon* at 20 to 40° C. It may contain more washing the impurities before vacuum drying the nine materials.

When the temperature of the vacuum drying is 20° C. or higher, the drying time can be prevented from becoming longer than necessary, and in the case of 40° C. or lower, some nutrients in the raw material are prevented from being destroyed or lost, according to the subsequent steps. It can maintain the antioxidant activity of processed herbal medicinal products.

According to an embodiment of the present invention, in the step (a), the *Leonurus japonicus* Houtt, *Dioscorea bulbifera*, *Solanum nigrum* L are vacuum dried at a temperature in a range of 20 to 25° C., and the *Scutellaria baicalensis*, *Akebiae Caulis*, corn silk, *Astragalus membranaceus* are vacuum dried at a temperature in a range of 30 to 35° C., The *Pueraria lobata* Ohwi, *Lithospermum erythrorhizon Pueraria lobata* Ohwi may be vacuum dried at a temperature in a range of 35 to 40° C. Specifically, by vacuum-drying each of the raw materials in the above-described temperature range, the antioxidant activity enhancement effect of the processed herbal medicinal product prepared according to a subsequent step may be improved.

According to embodiment of the present invention, step (a) may be performed by hot air drying at a vacuum pressure of 30 to 100 kPa. The vacuum pressure may mean a pressure inside the dryer or in a space to be dried.

When the vacuum pressure is 30 kPa or more, the pressure is too low to prevent the active ingredients of the raw materials from evaporating, and when the vacuum pressure is 100 kPa or less, the drying efficiency of the raw materials can be improved.

As a specific example, it may be 50 to 90 kPa, or 70 to 80 kpa, but is not limited thereto. In the present invention, the unit kPa may mean kPa·abs (kPa·absolute).

By removing moisture in the raw materials through the vacuum drying, the moisture content of each raw material can be reduced to 10% or less, 5% or less, or 3% or less. As a specific example, the moisture content of each raw material after vacuum drying may be 0.1 to 10%, 0.3 to 5%, or 0.5 to 3%, but is not limited thereto.

When the moisture content is 0.1% or more, it is possible to prevent the loss of the nutrient components of the raw material, and when the moisture content is less than 10%, the crushing process in the subsequent step (b) is easy, and by reducing the moisture content of the raw material, risk of corruption and spoilage can be avoided.

If the drying method is performed within the above temperature range, a drying method commonly used in the industry may be used, and as a non-limiting example, hot air drying, sun drying, or freeze drying may be used.

As a specific example, the drying may be hot air drying. In this case, problems such as an increase in space occupancy, influence of climate, delay in drying time, difficulty in mass production, etc., which occur during sun drying, can be solved. In addition, loss of nutrients and loss of raw materials generated during freeze drying can be solved. Problems such as lower freshness of raw materials can be solved, too.

That is, there is an effect that mass production is facilitated by reducing the space occupancy and drying time while improving the nutritional component retention characteristics and freshness of the raw material through the hot air drying.

As a specific example, the vacuum drying may be performed under vacuum conditions in an enclosed space in which internal heat does not leak. As a more specific example, it may be performed by hot air supplied in the closed space under vacuum conditions.

According to an embodiment of the present invention, the above-described vacuum drying may be performed for 1 to 48 hours, 3 to 40 hours, 5 to 30 hours, or 3 to 20 hours, but is not limited thereto.

The vacuum drying time may be performed until the moisture content of the raw materials becomes 10% or less, and by performing vacuum drying without exceeding the time to reach the moisture content, unnecessary energy consumption may be reduced.

According to an embodiment of the present invention, in step (b), the particle diameter of the powder may be 100 to 500 µm, 100 to 400 µm, 100 to 300 µm, or 150 to 250 µm. When the particle diameter of the powder is within the above range, there is an effect of improving the disintegration of the processed herbal medicine food.

Medicines have the advantage that the active ingredient continuously acts and does not deteriorate easily, but there may be a disadvantage in that disintegration is lowered as moisture is evaporated and hardened during the storage process.

Disintegration may mean the degree to which a medicine breaks down into a particle size in the body and dissolves. In other words, the short disintegration time may mean that the medicine dissolves quickly and is easily absorbed in the body, so that the active ingredient in the medicine is easily absorbed.

Accordingly, in the present invention, it was confirmed that the disintegration degree was improved by controlling the particle diameter of the powder within the above range to form a ring shape. In particular, it was confirmed that the effect of improving the disintegration degree was maintained even after long-term storage of the processed herbal medicinal product, and excellent long-term storage.

According to an embodiment of the present invention, in the step (c), the powder of each of the grinded raw materials is, the *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi, and *Lithospermum erythrorhizon* may be mixed in a weight ratio of 1:1.3 to 1.8:1.3 to 1.8:0.8 to 1.2:0.5 to 1.2:0.5 to 1.2:0.5 to 1.2:0.5 to 1.2:0.8 to 1.1.

In addition, as a specific example, the powders of each of the *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi, and *Lithospermum erythrorhizon* may be mixed in a weight ratio of 1:1.4 to 1.6:1.4 to 1.6:0.9 to 1.1:0.9 to 1.1:0.9 to 1.1:0.9 to 1.1:0.9 to 1.1.

When the powders of the nine raw materials are mixed in the weight ratio range described above, the taste, odor, color and overall preference of the processed herbal medicine are excellent, and thus palatability is improved.

According to an embodiment of the present invention, the step (c) is a step of mixing the powders of each of the grinded raw materials into a round shape, and by molding the powder into a round shape so that it is easy to take, the convenience of food may be maximized.

As a non-limiting example, the medicine may be prepared using a grinder after adding an excipient to the powder mixture. As the excipient, honey, gelatin, or starch-containing grains or powders of plants may be used. In addition, it may be molded into a ring shape by a conventional method.

According to an embodiment of the present invention, it may further comprise drying the molded round shape medicine in a dryer. The drying of the round shape medicine may be preferably naturally dried in order to prevent loss and destruction of active ingredients of the raw material.

According to an embodiment of the present invention, it may further comprise coating a film on the outer surface of the molded ring or the round shape medicine which has been formed and then dried. By coating the film, it is possible to prevent the shape of the medicine from being deformed due to external impact or the like.

The coating of the film may be performed using honey, starch syrup, sugar oligosaccharide, gluten, dextrin, gelatin, agar, gum arabic, etc., and a commonly used coating method may be used, but spray coating may be preferable.

According to the present invention, it relates to a natural processed food, and more particularly, it is possible to provide a method of manufacturing a processed herbal food that has excellent nutritional properties of the herbal medicine and maximizes the convenience of edible food.

Hereinafter, the present invention will be described in more detail by examples. However, the following examples are intended to illustrate the present invention, and that various changes and modifications are possible within the scope of the present invention and the scope of the technical idea is obvious to those skilled in the art, and the scope of the present invention is not limited thereto.

EXEMPLARY EMBODIMENT

Exemplary Embodiments 1 to 21

*Leonurus japonicus* Houtt (Republic of Korea), *Dioscorea bulbifera* (Republic of Korea: Hwasun, Jeonnam), *Solanum nigrum* L (Republic of Korea: Hwasun, Jeonnam), *Scutellaria baicalensis* (Republic of Korea), *Akebiae Caulis* (Republic of Korea), corn silk (Republic of Korea), *astragalus* (Republic of Korea), *Pueraria lobata* Ohwi (Republic of Korea) and *Lithospermum erythrorhizon* (Republic of Korea) are all prepared by washing all raw materials. Thereafter, the washed nine raw materials were vacuum dried. At this time, the vacuum drying was performed by hot air drying at a vacuum pressure of 80 kPa.

Thereafter, each of the vacuum-dried raw materials was grinded using a cutter mill to obtain a powder having a particle diameter of 250 µm.

Thereafter, the powder of each of the grinded raw materials, *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi and *Lithospermum erythrorhizon* were mixed with as weight ratio of 1.0:1.5:1.5:1.0:1.0:1.0:1.0:1.0:1.0 to obtain a mixed powder, 2t parts by weight of honey and 1 part by weight of dextrin were added and kneaded with respect to 100 parts by weight of the mixed powder, and then molded into a shape of a medicine using a medicine maker (a grinder) to prepare a processed herbal medicine.

Table 1 below shows the temperatures at the time of vacuum drying of the washed 9 raw materials according to Exemplary Embodiments 1 to 21.

TABLE 1 unit: ° C.

| Exemplary Embodiment | Leonurus japonicus Houtt | Dioscorea bulbifera | Solanum nigrum L | Scutellaria baicalensis | Akebiae Caulis | corn silk | Astragalus membranaceus | Pueraria lobata Ohwi | Lithospermum erythrorhizon |
|---|---|---|---|---|---|---|---|---|---|
| 1  | 20 | 20 | 20 | 30 | 30 | 30 | 30 | 35 | 35 |
| 2  | 23 | 24 | 22 | 32 | 33 | 33 | 34 | 38 | 36 |
| 3  | 25 | 25 | 25 | 35 | 35 | 35 | 35 | 40 | 40 |
| 4  | 18 | 24 | 22 | 32 | 33 | 33 | 34 | 38 | 36 |
| 5  | 27 | 24 | 22 | 32 | 33 | 33 | 34 | 38 | 36 |
| 6  | 23 | 18 | 22 | 32 | 33 | 33 | 34 | 38 | 36 |
| 7  | 23 | 27 | 22 | 32 | 33 | 33 | 34 | 38 | 36 |
| 8  | 23 | 24 | 18 | 32 | 33 | 33 | 34 | 38 | 36 |
| 9  | 23 | 24 | 27 | 32 | 33 | 33 | 34 | 38 | 36 |
| 10 | 23 | 24 | 22 | 28 | 33 | 33 | 34 | 38 | 36 |
| 11 | 23 | 24 | 22 | 37 | 33 | 33 | 34 | 38 | 36 |
| 12 | 23 | 24 | 22 | 32 | 28 | 33 | 34 | 38 | 36 |
| 13 | 23 | 24 | 22 | 32 | 37 | 33 | 34 | 38 | 36 |
| 14 | 23 | 24 | 22 | 32 | 33 | 28 | 34 | 38 | 36 |
| 15 | 23 | 24 | 22 | 32 | 33 | 37 | 34 | 38 | 36 |
| 16 | 23 | 24 | 22 | 32 | 33 | 33 | 28 | 38 | 36 |
| 17 | 23 | 24 | 22 | 32 | 33 | 33 | 37 | 38 | 36 |
| 18 | 23 | 24 | 22 | 32 | 33 | 33 | 34 | 33 | 36 |
| 19 | 23 | 24 | 22 | 32 | 33 | 33 | 34 | 42 | 36 |
| 20 | 23 | 24 | 22 | 32 | 33 | 33 | 34 | 38 | 33 |
| 21 | 23 | 24 | 22 | 32 | 33 | 33 | 34 | 38 | 42 |

Exemplary Embodiments 22-53

In Exemplary Embodiment 2, it was carried out in the same manner as in Exemplary Embodiment 2, except that the mixed ratio (weight ratio) of each grinded raw material powder was varied to obtain a mixed powder.

Table 2 below shows the mixed ratio (weight ratio) of the raw material powder according to Exemplary Embodiments 22 to 53.

unit: weight ratio

| Exemplary Embodiment | Leonurus japonicus Houtt | Dioscorea bulbifera | Solanum nigrum L | Scutellaria baicalensis | Akebiae Caulis | corn silk | Astragalus membranaceus | Pueraria lobata Ohwi | Lithospermum erythrorhizon |
|---|---|---|---|---|---|---|---|---|---|
| 22 | 1.0 | 1.3 | 1.5 | 1.0 | 1.0 | 1.0 | 1.0 | 1.0 | 1.0 |
| 23 | 1.0 | 1.8 | 1.5 | 1.0 | 1.0 | 1.0 | 1.0 | 1.0 | 1.0 |
| 24 | 1.0 | 1.1 | 1.5 | 1.0 | 1.0 | 1.0 | 1.0 | 1.0 | 1.0 |
| 25 | 1.0 | 2.0 | 1.5 | 1.0 | 1.0 | 1.0 | 1.0 | 1.0 | 1.0 |
| 26 | 1.0 | 1.5 | 1.3 | 1.0 | 1.0 | 1.0 | 1.0 | 1.0 | 1.0 |
| 27 | 1.0 | 1.5 | 1.8 | 1.0 | 1.0 | 1.0 | 1.0 | 1.0 | 1.0 |
| 28 | 1.0 | 1.5 | 1.1 | 1.0 | 1.0 | 1.0 | 1.0 | 1.0 | 1.0 |
| 29 | 1.0 | 1.5 | 2.0 | 1.0 | 1.0 | 1.0 | 1.0 | 1.0 | 1.0 |
| 30 | 1.0 | 1.5 | 1.5 | 0.8 | 1.0 | 1.0 | 1.0 | 1.0 | 1.0 |
| 31 | 1.0 | 1.5 | 1.5 | 1.2 | 1.0 | 1.0 | 1.0 | 1.0 | 1.0 |
| 32 | 1.0 | 1.5 | 1.5 | 0.6 | 1.0 | 1.0 | 1.0 | 1.0 | 1.0 |
| 33 | 1.0 | 1.5 | 1.5 | 1.4 | 1.0 | 1.0 | 1.0 | 1.0 | 1.0 |
| 34 | 1.0 | 1.5 | 1.5 | 1.0 | 0.5 | 1.0 | 1.0 | 1.0 | 1.0 |
| 35 | 1.0 | 1.5 | 1.5 | 1.0 | 1.2 | 1.0 | 1.0 | 1.0 | 1.0 |
| 36 | 1.0 | 1.5 | 1.5 | 1.0 | 0.3 | 1.0 | 1.0 | 1.0 | 1.0 |
| 37 | 1.0 | 1.5 | 1.5 | 1.0 | 1.4 | 1.0 | 1.0 | 1.0 | 1.0 |
| 38 | 1.0 | 1.5 | 1.5 | 1.0 | 1.0 | 0.5 | 1.0 | 1.0 | 1.0 |
| 39 | 1.0 | 1.5 | 1.5 | 1.0 | 1.0 | 1.2 | 1.0 | 1.0 | 1.0 |
| 40 | 1.0 | 1.5 | 1.5 | 1.0 | 1.0 | 0.3 | 1.0 | 1.0 | 1.0 |
| 41 | 1.0 | 1.5 | 1.5 | 1.0 | 1.0 | 1.4 | 1.0 | 1.0 | 1.0 |
| 42 | 1.0 | 1.5 | 1.5 | 1.0 | 1.0 | 1.0 | 0.5 | 1.0 | 1.0 |
| 43 | 1.0 | 1.5 | 1.5 | 1.0 | 1.0 | 1.0 | 1.2 | 1.0 | 1.0 |
| 44 | 1.0 | 1.5 | 1.5 | 1.0 | 1.0 | 1.0 | 0.3 | 1.0 | 1.0 |
| 45 | 1.0 | 1.5 | 1.5 | 1.0 | 1.0 | 1.0 | 1.4 | 1.0 | 1.0 |
| 46 | 1.0 | 1.5 | 1.5 | 1.0 | 1.0 | 1.0 | 1.0 | 0.5 | 1.0 |
| 47 | 1.0 | 1.5 | 1.5 | 1.0 | 1.0 | 1.0 | 1.0 | 1.2 | 1.0 |
| 48 | 1.0 | 1.5 | 1.5 | 1.0 | 1.0 | 1.0 | 1.0 | 0.3 | 1.0 |

-continued

| | | | | | | | | unit: weight ratio | |
|---|---|---|---|---|---|---|---|---|---|
| Exemplary Embodiment | Leonurus japonicus Houtt | Dioscorea bulbifera | Solanum nigrum L | Scutellaria baicalensis | Akebiae Caulis | corn silk | Astragalus membranaceus | Pueraria lobata Ohwi | Lithospermum erythrorhizon |
| 49 | 1.0 | 1.5 | 1.5 | 1.0 | 1.0 | 1.0 | 1.0 | 1.4 | 1.0 |
| 50 | 1.0 | 1.5 | 1.5 | 1.0 | 1.0 | 1.0 | 1.0 | 1.0 | 0.8 |
| 51 | 1.0 | 1.5 | 1.5 | 1.0 | 1.0 | 1.0 | 1.0 | 1.0 | 1.1 |
| 52 | 1.0 | 1.5 | 1.5 | 1.0 | 1.0 | 1.0 | 1.0 | 1.0 | 0.6 |
| 53 | 1.0 | 1.5 | 1.5 | 1.0 | 1.0 | 1.0 | 1.0 | 1.0 | 1.3 |

Exemplary Embodiment 54

In Exemplary Embodiment 54, it was carried out in the same manner as in Exemplary Embodiment 2, except that the vacuum-dried raw materials were each grinded to obtain a powder having a particle diameter of 100 μm instead of 250 μm.

Exemplary Embodiment 55

In Exemplary Embodiment 55, it was carried out in the same manner as in Exemplary Embodiment 2, except that the vacuum-dried raw materials were each grinded to obtain a powder having a particle diameter of 500 μm instead of 250 μm.

Exemplary Embodiment 56

In Exemplary Embodiment 56, it was carried out in the same manner as in Exemplary Embodiment 2, except that the vacuum-dried raw materials were each grinded to obtain a powder having a particle diameter of 50 μm instead of 250 μm.

Exemplary Embodiment 57

In Exemplary Embodiment 57, it was carried out in the same manner as in Exemplary Embodiment 2, except that the vacuum-dried raw materials were each grinded to obtain a powder having a particle diameter of 80 μm instead of 250 μm.

Exemplary Embodiment 58

In Exemplary Embodiment 58, it was carried out in the same manner as in Exemplary Embodiment 2, except that the vacuum-dried raw materials were each grinded to obtain a powder having a particle diameter of 550 μm instead of 250 μm.

Exemplary Embodiment 59

In Exemplary Embodiment 59, the vacuum-dried raw materials were each grinded to obtain a powder having a particle diameter of 600 μm instead of 250 μm, and it was carried out in the same manner as in Exemplary Embodiment 2.

COMPARATIVE EXAMPLE

Comparative Example 1

In Comparative Example 1, it was carried out in the same manner as in Example 2, except that the vacuum drying temperature of the nine washed raw materials was all at 15° C.

Comparative Example 2

In Comparative Example 2, it was carried out in the same manner as in Example 2, except that the vacuum drying temperature of the nine washed raw materials was all at 50° C.

EXPERIMENTAL EXAMPLE

Experimental Example 1—Antioxidant Activity Measurement (1) Manufacture of Antioxidant Activity Measurement Sample Samples were prepared as follows in order to measure the antioxidant activity of the processed herbal medicine products prepared from Exemplary Embodiments 1 to 21 and Comparative Examples 1 to 2.

First, after extracting for 7 hours at 200 rpm in a shaking incubator (SI-18, Jeio Tech., Daejeon, Korea) adjusted to 30° C. by adding 10 times the amount of 70% ethanol to each of the processed herbal foods of above Exemplary Embodiments and Comparative Examples, the supernatant fluid was filtered and concentrated with Whatman No.1 filter paper (Whatman, London, England), and then extracts of the supernatant fluid at concentrations of 25, 50 and 100 mg/mL were used as samples for antioxidant experiments, and as a positive control, BHA (Butylated hydroxyanisole) 50 ppm was used.

(2) DPPH Free Radical Scavenging Activity Experiment 1,1-diphenyl-2-picrylhydrazyl (DPPH) free radical scavenging activity was measured by modifying the Blois (26) method. The 0.4 mM DPPH solution was diluted with ethanol so that the absorbance at 517 nm became 1.0±0.05. Thereafter, 0.9 mL of the diluted DPPH solution was added to 0.1 mL of the prepared sample, stirred, and reacted in the dark at room temperature for 20 minutes, and then measured absorbance at 517 nm using a UV spectrophotometer (GENios-basic, Tecan, Groedig, Austria), and then DPPH free radical scavenging activity was calculated from the following calculation formula 1, and is shown in Table 3 as follows.

DPPH radical (%)={1−(experimental group sample O.D/control group sample O.D)}×100, wherein O.D is Optical Density     [Formula 2]

(3) ABTS Cation Radical Scavenging Activity Experiment 2,2'-azinobis(3-ethylbenzothiazoline-6-sulfonic acid) (ABTS) cation radical scavenging activity was measured by applying the method of Pellegrin (27). After mixing equal amounts of 7 mM ABTS and 2.6 mM potassium persulfide ($K_2S_2O_8$), the mixed solution were left in the dark for 24 hours to form a greenish-blue chromophore, and this solution was diluted with distilled water so that the absorbance value was 0.7-0.8 at 735 nm. 190 μL of the diluted ABTS solution and 10 μL of the sample solution were mixed and incubated for 5 minutes, and the absorbance was measured at 734 nm, and then ABTS cation radical scavenging activity was calculated from the following calculation formula 2, and is shown in Table 3 as follows.

ABTS radical (%)={1−(experimental group sample O.D/control group sample O.D)}×100, wherein O.D is Optical Density　　　　　　　　　　　　　　　　　　[Formula 2]

TABLE 3

| | DPPH radical scavenging activity (%) | | | ABTS radical scavenging activity (%) | | |
|---|---|---|---|---|---|---|
| | concentration (mg/mL) | | | | | |
| | 25 | 50 | 100 | 25 | 50 | 100 |
| Exemplary Embodiment 1 | 43.1 | 74.8 | 86.2 | 87.8 | 91.8 | 93.0 |
| Exemplary Embodiment 2 | 41.0 | 76.7 | 85.9 | 88.0 | 92.4 | 93.5 |
| Exemplary Embodiment 3 | 41.8 | 74.6 | 86.0 | 88.8 | 90.5 | 92.4 |
| Exemplary Embodiment 4 | 26.1 | 34.5 | 69.3 | 55.1 | 63.8 | 76.0 |
| Exemplary Embodiment 5 | 19.9 | 34.7 | 59.4 | 48.1 | 51.9 | 70.1 |
| Exemplary Embodiment 6 | 22.8 | 38.0 | 68.1 | 53.0 | 59.9 | 74.8 |
| Exemplary Embodiment 7 | 20.1 | 30.1 | 58.7 | 44.5 | 50.4 | 64.7 |
| Exemplary Embodiment 8 | 25.0 | 38.8 | 70.2 | 52.8 | 61.7 | 73.5 |
| Exemplary Embodiment 9 | 16.6 | 29.3 | 57.9 | 46.8 | 54.1 | 69.9 |
| Exemplary Embodiment 10 | 24.2 | 35.0 | 66.5 | 50.6 | 64.8 | 75.3 |
| Exemplary Embodiment 11 | 19.6 | 32.0 | 60.2 | 49.7 | 55.0 | 68.1 |
| Exemplary Embodiment 12 | 26.8 | 37.1 | 71.1 | 56.8 | 66.0 | 77.5 |
| Exemplary Embodiment 13 | 18.5 | 33.8 | 61.7 | 44.5 | 57.7 | 66.6 |
| Exemplary Embodiment 14 | 24.0 | 39.5 | 72.8 | 57.1 | 65.1 | 76.7 |
| Exemplary Embodiment 15 | 18.0 | 35.1 | 59.9 | 43.5 | 54.2 | 70.1 |
| Exemplary Embodiment 16 | 20.8 | 33.8 | 65.8 | 52.9 | 63.0 | 70.9 |
| Exemplary Embodiment 17 | 16.9 | 30.1 | 55.0 | 43.9 | 59.8 | 69.4 |
| Exemplary Embodiment 18 | 20.7 | 32.9 | 64.6 | 55.5 | 64.8 | 74.7 |
| Exemplary Embodiment 19 | 19.3 | 33.1 | 60.8 | 49.9 | 54.3 | 64.8 |
| Exemplary Embodiment 20 | 24.1 | 38.7 | 67.7 | 54.8 | 63.7 | 75.0 |
| Exemplary Embodiment 21 | 18.8 | 31.3 | 58.3 | 50.1 | 53.9 | 66.1 |
| comparative example 1 | 13.6 | 20.6 | 38.0 | 38.2 | 44.7 | 59.3 |
| comparative example 2 | 10.9 | 15.4 | 28.4 | 33.1 | 39.1 | 54.0 |

Referring to Table 3, Exemplary Embodiments 1 to 21 in which the temperature during vacuum drying of the nine raw materials is within an appropriate range (20 to 40° C.) have significantly higher DPPH radical scavenging activity and ABTS radical scavenging activity than those of Comparative Exemplary Embodiments 1 and 2 outside the appropriate range.

In particular, among the nine types of raw materials, Exemplary Embodiments 1 to 3, which contain *Leonurus japonicus* Houtt, *Dioscorea bulbifera*, and *Solanum nigrum* L vacuum-dried at a temperature in a range of 20 to 25° C., which contain *Scutellaria baicalensis*, *Akebiae Caulis*, corn silk, and *Astragalus membranaceus* vacuum-dried at a temperature in a range of 30 to 35° C., which contain *Pueraria lobata* Ohwi, *Lithospermum erythrorhizon* vacuum-dried at a temperature in a range of 35 to 40° C. have significantly higher DPPH radical scavenging activity and ABTS radical scavenging activity than those of Exemplary Embodiments 4 to 21 outside the vacuum drying temperature range for each raw materials.

Through this, it was confirmed that there is an effect of enhancing the antioxidant activity of processed herbal medicine products when the nine raw material powders of the present invention are vacuum-dried in an appropriate temperature range according to the present invention.

Experimental Example 2—Disintegration and Long-Term Storage Test

The disintegration of the processed herbal medicine products prepared in Exemplary Embodiments 2 and Exemplary Embodiments 54 to 59 was measured. The disintegration test is a test method that checks whether or not the granules disintegrate within a prescribed time in a prescribed condition among tablets, granules, pills, and suppositories in the test solution under the same conditions as the digestive function of the human body. The above processed herbal medicine products were tested according to the Food Code 10-9-13 disintegration test method (the 8th revised disintegration test method of the Korean Pharmacopoeia).

Table 4 shows the results of predicting the absorption of the round shape pills in the body by measuring 50 g of the processed herbal medicinal product in 100 g of water and then measuring the dissolution time in units of 30 seconds, 60 seconds, 180 seconds, and 300 seconds.

In addition, in Table 5, the degree of disintegration of the processed herbal medicine product of the above exemplary embodiments stored at 35° C. for 30 days was confirmed by the same method as described above, and the results are shown.

TABLE 4

| | disintegration time(second) | | | |
|---|---|---|---|---|
| | 30 | 60 | 180 | 300 |
| Exemplary Embodiments 2 | disintegration starts | 3/4 disintegration | 100% disintegration | 100% disintegration |
| Exemplary Embodiments 54 | disintegration starts | 3/4 disintegration | 100% disintegration | 100% disintegration |
| Exemplary Embodiments 55 | disintegration starts | 2/4 disintegration | 3/4 disintegration | 100% disintegration |
| Exemplary Embodiments 56 | disintegration starts | 1/4 disintegration | 2/4 disintegration | 3/4 disintegration |
| Exemplary Embodiments 57 | disintegration starts | 1/4 disintegration | 2/4 disintegration | 3/4 disintegration |
| Exemplary Embodiments 58 | non disintegration | non disintegration | 1/3 disintegration | 2/3 disintegration |
| Exemplary Embodiments 59 | non disintegration | non disintegration | 1/3 disintegration | 2/3 disintegration |

Referring to Table 4, Exemplary Embodiments 2 and 54 to 55 in which the diameters of the nine raw material powder particles are pulverized in an appropriate range (100 to 500 μm) have significantly faster disintegration time compared to Exemplary Embodiments 56 to 59 outside the appropriate range. Through this, when the nine raw material powders of the present invention have a particle diameter within the above range, it can be predicted that the absorption time in the body will be fast.

TABLE 5

| | disintegration time(second) | | | |
|---|---|---|---|---|
| | 30 | 60 | 180 | 300 |
| Exemplary Embodiments 2 | disintegration starts | 3/4 disintegration | 100% disintegration | 100% disintegration |
| Exemplary Embodiments 54 | disintegration starts | 3/4 disintegration | 100% disintegration | 100% disintegration |
| Exemplary Embodiments 55 | disintegration starts | 2/4 disintegration | 3/4 disintegration | 100% disintegration |
| Exemplary Embodiments 56 | disintegration starts | 1/4 disintegration | 2/4 disintegration | 3/4 disintegration |
| Exemplary Embodiments 57 | disintegration starts | 1/4 disintegration | 2/4 disintegration | 3/4 disintegration |
| Exemplary Embodiments 58 | non disintegration | non disintegration | 1/3 disintegration | 2/3 disintegration |
| Exemplary Embodiments 59 | non disintegration | non disintegration | 1/3 disintegration | 2/3 disintegration |

Referring to Table 5, it was confirmed that the same disintegration time as in Table 4 was measured even after storing the processed herbal medicinal product of the embodiment for 30 days at 35° C., and thus maintaining the disintegration characteristics even after long-term storage period.

Through this, when the nine raw material powders of the present invention are pulverized into a particle size of an appropriate diameter range (100 to 500 μm) according to the present invention, it was confirmed that the characteristics of long-term storage of the processed herbal medicine food are excellent.

Experimental Example 3—Sensory Test

A sensory test was performed on the processed herbal medicine products prepared from Exemplary Embodiment 2 and Exemplary Embodiments 22 to 53. A total 40 testers including 20 sensory professional testers (10 males and 10 females) who have gone through the sensory test training course and 20 general adults (10 males and 10 females) who are recognized as having no problems with the sense of smell (non-smoker, healthy people does not catch a cold), were selected to evaluate taste, smell, color and overall acceptability, and the results are shown in Table 6 below. For each item, a rating method on a 9-point scale (the closer to 9 points, the better the taste, smell, color, and overall preference), and the average of the results of the rating method was calculated and shown.

TABLE 6

| | Taste | Smell | Color | Overall palatability |
|---|---|---|---|---|
| Exemplary Embodiment 2 | 7.8 | 8.7 | 6.9 | 8.6 |
| Exemplary Embodiment 22 | 7.6 | 8.3 | 6.8 | 8.2 |

TABLE 6-continued

| | Taste | Smell | Color | Overall palatability |
|---|---|---|---|---|
| Exemplary Embodiment 23 | 8.0 | 8.2 | 6.2 | 8.4 |
| Exemplary Embodiment 24 | 6.1 | 6.9 | 5.0 | 6.1 |
| Exemplary Embodiment 25 | 5.7 | 7.3 | 5.6 | 6.4 |
| Exemplary Embodiment 26 | 7.9 | 8.2 | 6.7 | 8.4 |
| Exemplary Embodiment 27 | 7.8 | 8.1 | 6.8 | 8.5 |
| Exemplary Embodiment 28 | 6.2 | 6.5 | 5.8 | 6.6 |
| Exemplary Embodiment 29 | 6.6 | 6.4 | 5.4 | 6.5 |
| Exemplary Embodiment 30 | 7.7 | 8.2 | 7.0 | 8.5 |
| Exemplary Embodiment 31 | 7.6 | 7.9 | 7.3 | 8.4 |
| Exemplary Embodiment 32 | 5.8 | 6.8 | 5.2 | 6.1 |
| Exemplary Embodiment 33 | 5.1 | 6.8 | 4.9 | 6.5 |
| Exemplary Embodiment 34 | 8.1 | 8.2 | 7.4 | 8.2 |
| Exemplary Embodiment 35 | 7.8 | 8.1 | 6.5 | 8.0 |
| Exemplary Embodiment 36 | 5.6 | 6.7 | 5.0 | 6.2 |
| Exemplary Embodiment 37 | 5.4 | 7.6 | 4.8 | 6.9 |
| Exemplary Embodiment 38 | 7.7 | 8.5 | 6.6 | 8.3 |
| Exemplary Embodiment 39 | 7.6 | 8.1 | 6.2 | 8.3 |
| Exemplary Embodiment 40 | 5.9 | 7.1 | 5.5 | 6.3 |
| Exemplary Embodiment 41 | 6.3 | 6.5 | 5.1 | 5.9 |
| Exemplary Embodiment 42 | 7.8 | 8.0 | 6.3 | 8.1 |
| Exemplary Embodiment 43 | 7.9 | 8.3 | 7.5 | 8.6 |
| Exemplary Embodiment 44 | 5.5 | 6.2 | 4.7 | 5.8 |
| Exemplary Embodiment 45 | 5.9 | 6.8 | 4.7 | 5.9 |
| Exemplary Embodiment 46 | 8.2 | 7.8 | 7.1 | 8.2 |
| Exemplary Embodiment 47 | 7.9 | 8.2 | 6.8 | 8.0 |
| Exemplary Embodiment 48 | 6.1 | 7.0 | 5.1 | 6.4 |
| Exemplary Embodiment 49 | 6.3 | 6.3 | 4.9 | 6.3 |
| Exemplary Embodiment 50 | 8.1 | 7.9 | 7.4 | 7.9 |
| Exemplary Embodiment 51 | 8.0 | 7.8 | 7.1 | 7.8 |
| Exemplary Embodiment 52 | 5.4 | 6.6 | 4.8 | 5.7 |
| Exemplary Embodiment 53 | 5.5 | 6.9 | 4.7 | 6.7 |

Referring table 6, it was confirmed that Exemplary Embodiments 22 to 23, 26 to 27, 30 to 31, 34 to 35, 38 to 39, 42 to 43, 46 to 47, and 50 to 51 of the processed herbal medicine food obtained mixture of powder which satisfies a appropriate range of a mixed ratio(w/w) that the mixed ratio(w/w) of the *Leonurus japonicus* Houtt, *Dioscorea bulbifera, Solanum nigrum* L, *Scutellaria baicalensis, Akebiae Caulis*, corn silk, *Astragalus membranaceus, Pueraria lobata* Ohwi, and *Lithospermum erythrorhizon* is 1:1.3 to 1.8:1.3 to 1.8:0.8 to 1.2:0.5 to 1.2:0.5 to 1.2:0.5 to 1.2:0.8 to 1.1 have higher point in taste, smell, color, overall palatability compared to Exemplary Embodiments 24 to 25, 28 to 29, 32 to 33, 36 to 37, 40 to 41, 44 to 45, 48 to 49, and 52 to 53 outside the appropriate range of the mixed ratio (w/w).

Through this, it was confirmed that when the nine raw material powders of the present invention are mixed in the appropriate mixed ratio range according to the present invention, there is an effect of improving the palatability of processed herbal medicine food.

What is claimed is:

1. A manufacturing method of herbal medicine processed food, the method comprising:
   (a) drying raw materials of *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi, and *Lithospermum erythrorhizon* by means of vacuum drying, wherein the drying temperature is 20 to 40° C.;
   (b) grinding each of the vacuum-dried raw material of step (a) to produce powders; and
   (c) shaping a mixture of powders of step (b) into a round shape.

2. The method of claim 1, wherein step (a) comprises:
   drying *Leonurus japonicus* Houtt, *Dioscorea bulbifera*, and *Solanum nigrum* L at a temperature in a range of 20 to 25° C.;
   drying *Scutellaria baicalensis*, *Akebiae Caulis*, corn silk, and *Astragalus membranaceus* at a temperature in a range of 30 to 35° C.; and
   drying *Pueraria lobata* Ohwi; and *Lithospermum erythrorhizon* at a temperature in a range of 35 to 40° C.

3. The method of claim 1, wherein step (a) comprises:
   drying by means of hot air at a vacuum pressure in a range of 30 to 100 kPa.

4. The method of claim 1, wherein step (b) comprises:
   a particle diameter of the powder is in a range of 100 to 500 μm.

5. The method of claim 1, wherein the mixture of powders in the step (c) comprises a ratio(w/w) of the *Leonurus japonicus* Houtt, *Dioscorea bulbifera*, *Solanum nigrum* L, *Scutellaria baicalensis*, *Akebiae Caulis*, corn silk, *Astragalus membranaceus*, *Pueraria lobata* Ohwi, and *Lithospermum erythrorhizon* of 1:1.3 to 1.8:1.3 to 1.8:0.8 to 1.2:0.5 to 1.2:0.5 to 1.2:0.5 to 1.2:0.5 to 1.2:0.8 to 1.1.

* * * * *